(12) United States Patent
Nishikawa et al.

(10) Patent No.: US 11,304,614 B2
(45) Date of Patent: Apr. 19, 2022

(54) BAG-SHAPED STRUCTURE, BLOOD PRESSURE MONITOR CUFF, AND BLOOD PRESSURE MONITOR

(71) Applicants: OMRON CORPORATION, Kyoto (JP); OMRON HEALTHCARE CO., LTD., Muko (JP)

(72) Inventors: Kazuyoshi Nishikawa, Ritto (JP); Shuhei Ojiro, Kyoto (JP)

(73) Assignees: OMRON CORPORATION; OMRON HEALTHCARE CO., LTD.

( * ) Notice: Subject to any disclaimer, the term of this patent is extended or adjusted under 35 U.S.C. 154(b) by 272 days.

(21) Appl. No.: 16/348,998

(22) PCT Filed: Dec. 26, 2017

(86) PCT No.: PCT/JP2017/046645
§ 371 (c)(1),
(2) Date: May 10, 2019

(87) PCT Pub. No.: WO2018/124072
PCT Pub. Date: Jul. 5, 2018

(65) Prior Publication Data
US 2019/0261871 A1    Aug. 29, 2019

(30) Foreign Application Priority Data
Dec. 27, 2016    (JP) .............................. JP2016-253811

(51) Int. Cl.
*B32B 27/08*    (2006.01)
*A61B 5/022*    (2006.01)
(Continued)

(52) U.S. Cl.
CPC .......... *A61B 5/02241* (2013.01); *A61B 5/022* (2013.01); *A61B 5/0225* (2013.01);
(Continued)

(58) Field of Classification Search
CPC . A61B 5/022; A61B 5/02233; A61B 5/02241; A61B 5/0225; A61B 5/6824;
(Continued)

(56) References Cited

U.S. PATENT DOCUMENTS 7,250,030 B2    7/2007    Sano et al.
2006/0129049 A1    6/2006    Sano et al.

FOREIGN PATENT DOCUMENTS

CN    201870635 U    6/2011
JP    H0728501 U    5/1995
(Continued)

OTHER PUBLICATIONS

International Search Report (in English and Japanese) and Written Opinion (in English and Japanese) issued in PCT/JP2017/046645, dated Mar. 20, 2018; ISA/JP.
(Continued)

*Primary Examiner* — Lawrence D Ferguson
(74) *Attorney, Agent, or Firm* — Harness, Dickey & Pierce, P.L.C.

(57) ABSTRACT

A bag-shaped structure excellent in vascular compressibility and creep resistance, and capable of reducing the processing cost, a blood pressure monitor cuff, and a blood pressure monitor is provided. A bag-shaped structure includes a first sheet member including a layer formed of a thermoplastic elastomer; and a second sheet member including a plurality of layers formed of a plurality of types of thermoplastic elastomers having different levels of hardness, wherein the second sheet member is joined with the first sheet member, and a layer, that is included in the plurality of layers of the second sheet member and that is in contact with a living body, has a Shore A hardness higher than a Shore A hardness of at least one of the other layers of the second sheet member.

4 Claims, 5 Drawing Sheets

(51) Int. Cl.
*B32B 7/022* (2019.01)
*B32B 27/40* (2006.01)
*A61B 5/0225* (2006.01)
*A61B 5/00* (2006.01)

(52) U.S. Cl.
CPC .......... *A61B 5/02233* (2013.01); *B32B 7/022* (2019.01); *B32B 27/08* (2013.01); *B32B 27/40* (2013.01); *A61B 5/6824* (2013.01); *B32B 2307/536* (2013.01); *B32B 2457/00* (2013.01)

(58) Field of Classification Search
CPC . B32B 1/02; B32B 2250/24; B32B 2307/536; B32B 2307/732; B32B 2457/00; B32B 2535/00; B32B 27/08; B32B 27/30; B32B 27/302; B32B 27/304; B32B 27/306; B32B 27/32; B32B 27/34; B32B 27/40; B32B 7/022; B32B 7/08; B32B 7/12
See application file for complete search history.

(56) References Cited

FOREIGN PATENT DOCUMENTS

| | | |
|---|---|---|
| JP | 2002360527 A | 12/2002 |
| JP | 2006158876 A | 6/2006 |
| JP | 200792217 A | 4/2007 |
| JP | 2010284517 A | 12/2010 |
| WO | 2014102873 A1 | 7/2014 |

OTHER PUBLICATIONS

Chinese Office Action for Application No. 201780068487.9 dated Apr. 8, 2021 with English translation (18 pages).
Japanese Office Action dated Aug. 25, 2020 (with English translation) (6 pages).
International Preliminary Report on Patentability issued in PCT/JP2017/046645, dated Jul. 2, 2019; ISA/JP (14 pages).
CA Japanese Office Action dated Feb. 25, 2020 (with English translation) (13 pages).

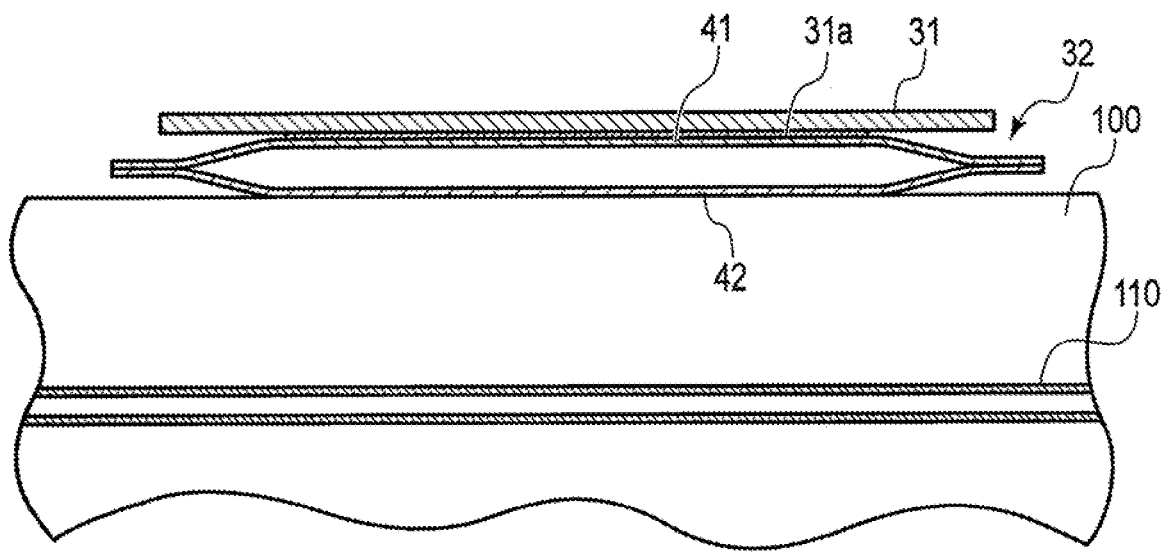
F I G. 5
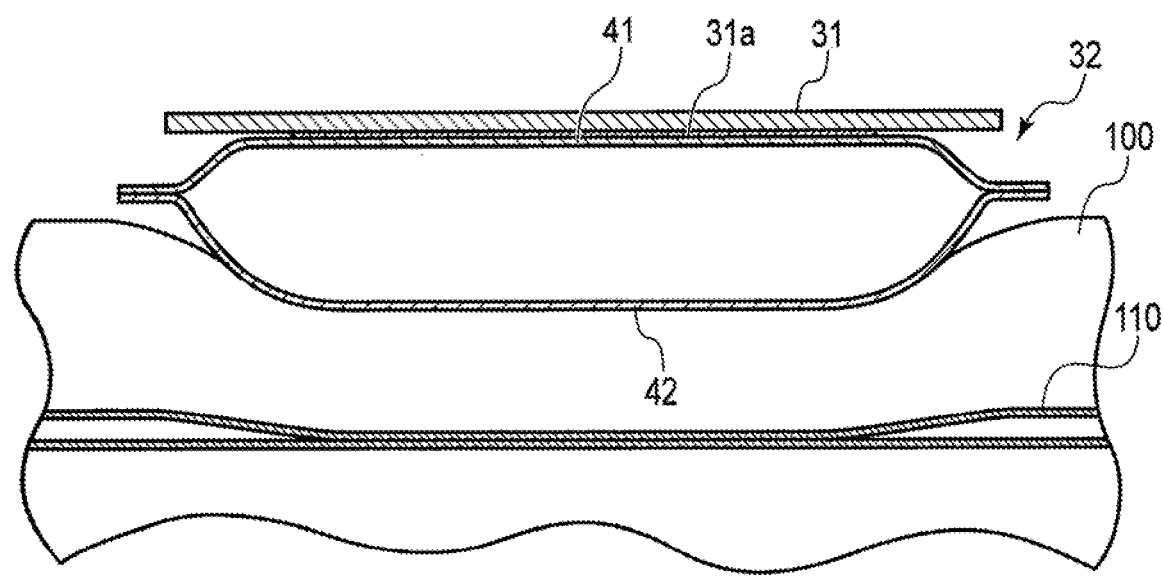
F I G. 6

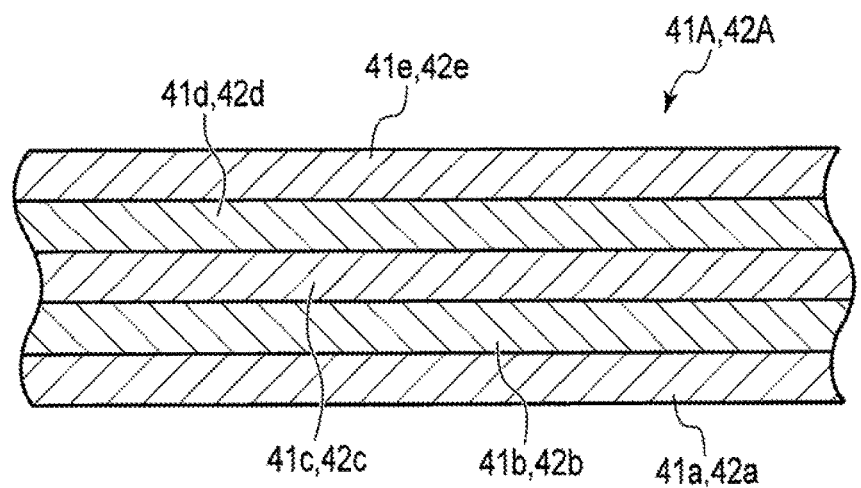
F I G. 7
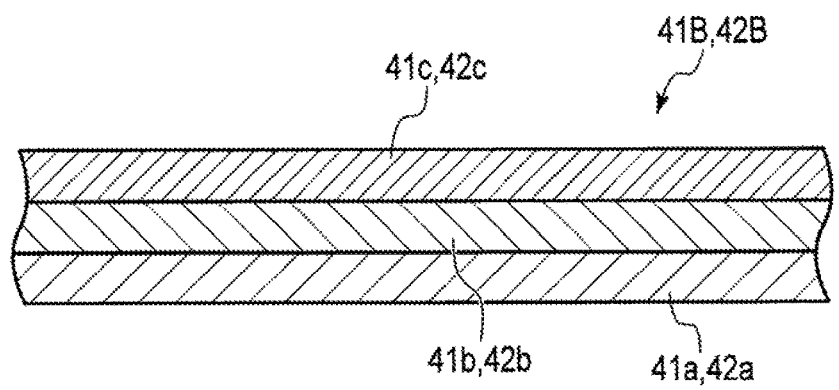
F I G. 8
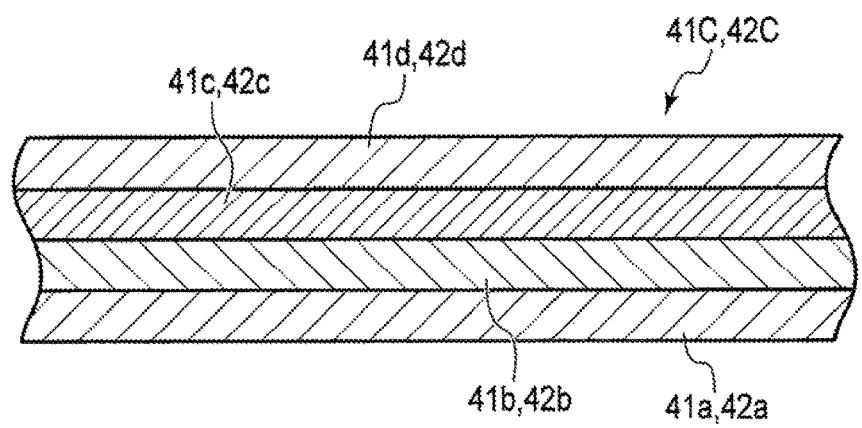
F I G. 9

BAG-SHAPED STRUCTURE, BLOOD PRESSURE MONITOR CUFF, AND BLOOD PRESSURE MONITOR

CROSS-REFERENCE TO RELATED APPLICATIONS

This is a U.S. National Stage Application under 35 U.S.C. 371 of International Application No. PCT/JP2017/046645 (not published in English), filed Dec. 26, 2017, which claims priority to Japanese Patent Application No. 2016-253811, filed Dec. 27, 2016. The disclosures of the above applications are incorporated herein by reference.

FIELD

The present invention relates to a bag-shaped structure that compresses a living body in measurement of blood pressure, a blood pressure monitor cuff, and a blood pressure monitor.

BACKGROUND

In recent years, a blood pressure monitor used for blood pressure measurement is utilized not only in medical facilities, but also in households as means for checking health conditions. A blood pressure monitor measures a blood pressure by detecting pulses generated in an artery and vibrations of an arterial wall, by wrapping a cuff including a bag-shaped structure around an upper arm or a wrist, etc. of a human body and by inflating and deflating the bag-shaped structure.

There is a demand for such a blood pressure monitor with a narrower cuff, to improve the ease of handling and to reduce the size of the cuff. However, the narrower cuff may incur the risk of inhibition in compression performance and blood flow impediment performance. There is also a known technique for providing a blood pressure monitor cuff suitable for reduction in width, while maintaining high compression performance and blood flow impediment performance (see, for example, Jpn. Pat. Appln. KOKAI Publication No. 2006-158876).

Such a blood pressure monitor cuff includes, when worn on a living body, a bag-shaped structure including a first bag located on the outer side as viewed in the direction of thickness and a second bag located on the inner side as viewed in the thickness direction. The second bag is formed on the inner side with respect to both ends of an inflation space of the first bag as viewed in the width direction, by joining a single-layer sheet member that forms an outer surface of the first bag on the side of the living body.

When such a bag-shaped structure is inflated, since a joint portion between the first bag and the second bag is provided on the inner side with respect to both ends of the inflation space of the first bag, as viewed in the width direction, not only do inflation of the first bag and inflation of the second bag occur, but also, through the inflation of the first bag, the joint portion travels toward the direction of the living body. This allows the blood pressure monitor cuff to uniformly and strongly compress the living body over a wide range of the living body, thus ensuring a long distance over which the artery is occluded, with respect to the width of the bag-shaped structure. It is therefore possible to achieve high compression performance and high blood flow impediment performance with a simple configuration, and to provide a blood pressure monitor cuff suitable for a reduced cuff width.

SUMMARY

In a typical blood pressure monitor cuff, a highly expandable and contractible material is used as a sheet member forming a bag-shaped structure, in order to provide satisfactory vascular compressibility. However, when a bag-shaped structure formed of a highly expandable and contractible material is repeatedly used, the bag-shaped structure may be slackened by creep. Under the circumstances, there is a demand for a bag-shaped structure capable of preventing the bag-shaped structure from being slackened even after repeated use, namely, excellent in creep resistance, which represents resistance to repeated use.

In addition, since the bag-shaped structure is formed of a first bag and a second bag, the number of joint portions increases. Since the cost for processing the bag-shaped structure increases as the number of joint portions increases, there is a demand for reduction in the processing cost of the bag-shaped structure.

It is therefore an object of the present invention to provide a bag-shaped structure, a blood pressure monitor cuff, and a blood pressure monitor excellent in vascular compressibility and creep resistance, and capable of reducing the processing cost.

According to a first aspect of the present invention, there is provided a bag-shaped structure including: a first sheet member including a layer formed of a thermoplastic elastomer; and a second sheet member including a plurality of layers formed of a plurality of types of thermoplastic elastomers having different levels of hardness, wherein the second sheet member is joined with the first sheet member, and a layer that is included in the plurality of layers of the second sheet member and that is in contact with a living body has a Shore A hardness higher than a Shore A hardness of at least one of the other layers of the second sheet member.

According to a second aspect of the present invention, there is provided a bag-shaped structure according to the first aspect, wherein the second sheet member includes three or more layers formed of a thermoplastic elastomer, and a third layer is included between a first layer that is in contact with the living body and a second layer that is in contact with the first sheet member, the third layer having a Shore A hardness lower than a Shore A hardness of the first and second layers.

According to a third aspect of the present invention, there is provided a bag-shaped structure according to the second aspect, wherein the first layer and the second layer are formed to have the same thickness, and the second sheet member is configured to have a layer composition ratio T1:T2:T1 ranging between 1:2:1 and 1:20:1, where T1 represents a thickness of each of the first layer and the second layer and T2 represents a thickness of the third layer.

According to a fourth aspect of the present invention, there is provided a bag-shaped structure according to the second aspect, wherein the second sheet member is configured in such a manner that the first layer and the second layer are formed of a thermoplastic elastomer having a Shore A hardness of 70 or higher, and the third layer is formed of a thermoplastic elastomer having a Shore A hardness of 65 or lower.

According to a fifth aspect of the present invention, there is provided a bag-shaped structure according to one of the first to fourth aspects, wherein the thermoplastic elastomer is formed of a thermoplastic polyurethane resin.

According to a sixth aspect of the present invention, there is provided a blood pressure monitor cuff including: the bag-shaped structure according to one of the first to fifth aspects; and a base material joined with the first sheet member.

According to a seventh aspect of the present invention, there is provided a blood pressure monitor including: a cuff including the bag-shaped structure according to one of the first to fifth aspects and a base material joined with the first sheet member; a pump that supplies compressed air to the bag-shaped structure; an on-off valve that deflates the bag-shaped structure inflated by the compressed air supplied by the pump; a pressure sensor that detects a pressure of the bag-shaped structure; and a controller that controls the pump and the on-off valve and obtains a blood pressure value based on information on the pressure detected by the pressure sensor.

According to the first aspect, a bag-shaped structure including a first sheet member and a second sheet member is configured in such a manner that a layer of the second sheet member that is in contact with a living body has a Shore A hardness higher than a Shore A hardness of at least one of the other layers of the second sheet member. With this configuration, the bag-shaped structure is adhered to the human skin when worn on a living body, thus inhibiting inflation of the bag-shaped structure and preventing reduction in vascular compressibility. It is thereby possible to obtain a bag-shaped structure excellent both in vascular compressibility and creep resistance, and to reduce the processing cost.

According to the second aspect, by including, between a first layer that is in contact with the living body and a second layer that is in contact with the first sheet member, an inner layer having a Shore A hardness lower than a Shore A hardness of the first layer and the second layer, the bag-shaped structure achieves high vascular compressibility.

According to the third aspect, by configuring the second sheet member to have a layer composition ratio T1:T2:T1 ranging between 1:2:1 and 1:20:1, high vascular compressibility and creep resistance are obtained.

According to the fourth aspect, the first layer and the second layer forming the outer layers of the second sheet member are formed of a thermoplastic elastomer having a Shore A hardness of 70 or higher, and the third layer forming the inner layer is formed of a thermoplastic elastomer having a Shore A hardness of 65 or lower. With this configuration, the bag-shaped structure achieves high vascular compressibility owing to the third layer, and achieves high creep resistance owing to the first and second layers.

According to the fifth aspect, long-term quality guarantee for use in a blood pressure monitor can be achieved, since a thermoplastic polyurethane resin used as the thermoplastic elastomer is excellent in material durability, namely, not easily hydrolyzed by sweat, hand cream, etc. or swollen by fat, etc. This is particularly advantageous in the case where the bag-shaped structure is used in a blood pressure monitor in direct contact with the living body.

According to the sixth aspect, by including the bag-shaped structure according to one of the first to fifth aspects, and a base material joined with the first sheet member, a blood pressure monitor cuff that produces one of the advantageous effects according to the first to fifth aspects is provided.

According to the seventh aspect, by including a cuff with the bag-shaped structure according to one of the first to fifth aspects, and including a base material joined with the first sheet member, a blood pressure monitor that produces one of the advantageous effects according to the first to fifth aspects is provided.

BRIEF DESCRIPTION OF THE DRAWINGS

FIG. 5 is a cross-sectional view showing a relationship between the cuff and a living body when the blood pressure monitor is worn on the living body.

FIG. 6 is a cross-sectional view showing a relationship between the cuff and the living body when the blood pressure monitor is used.

FIG. 7 is a cross-sectional view showing a configuration of a first sheet member and a second sheet member of a bag-shaped structure according to a first modification of the present invention.

FIG. 8 is a cross-sectional view showing a configuration of a first sheet member and a second sheet member of a bag-shaped structure according to a second modification.

FIG. 9 is a cross-sectional view showing a configuration of a first sheet member and a second sheet member of a bag-shaped structure according to a third modification.

DETAILED DESCRIPTION

First Embodiment

Hereinafter, a blood pressure monitor 1 including a cuff 12 with a bag-shaped structure 32 according to an embodiment of the present invention will be described with reference to FIGS. 1 to 6.

Figure 1:
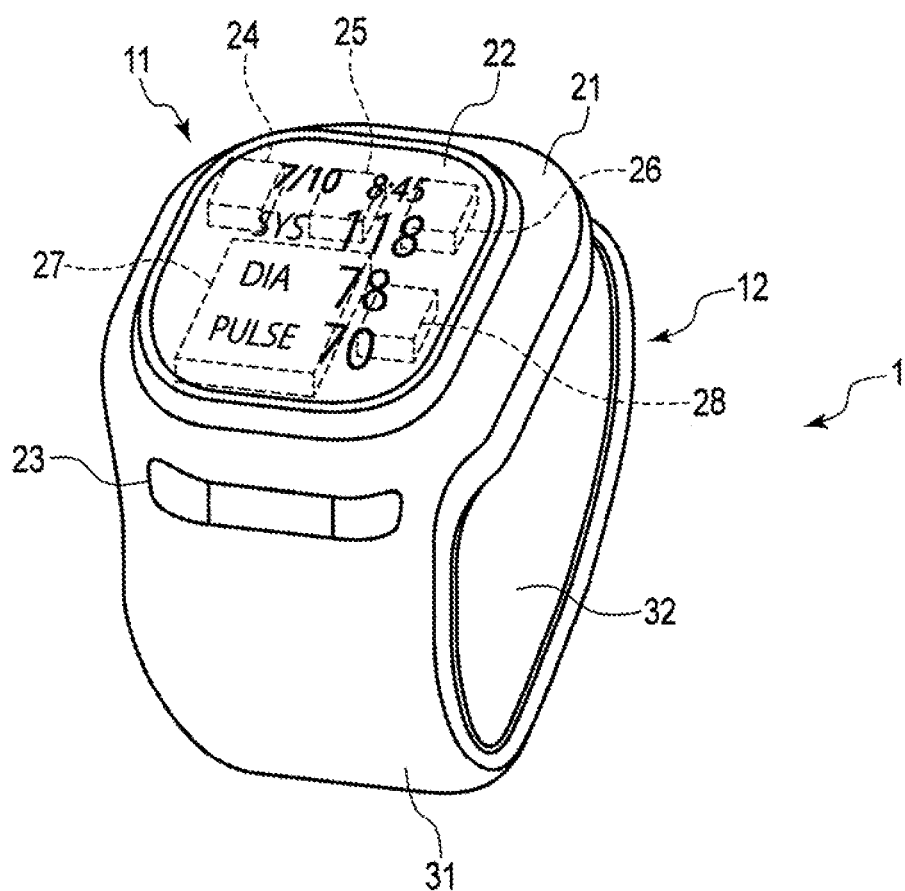
FIG. 1 is a perspective view showing a configuration of a blood pressure monitor according to one embodiment of the present invention.
Figure 2:
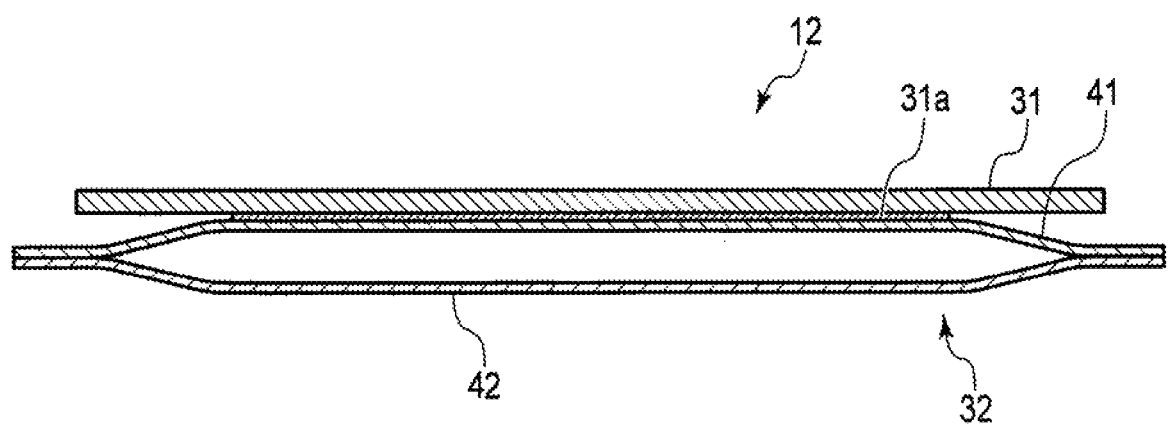
FIG. 2 is a cross-sectional view showing a configuration of a cuff used in the blood pressure monitor.
Figure 3:
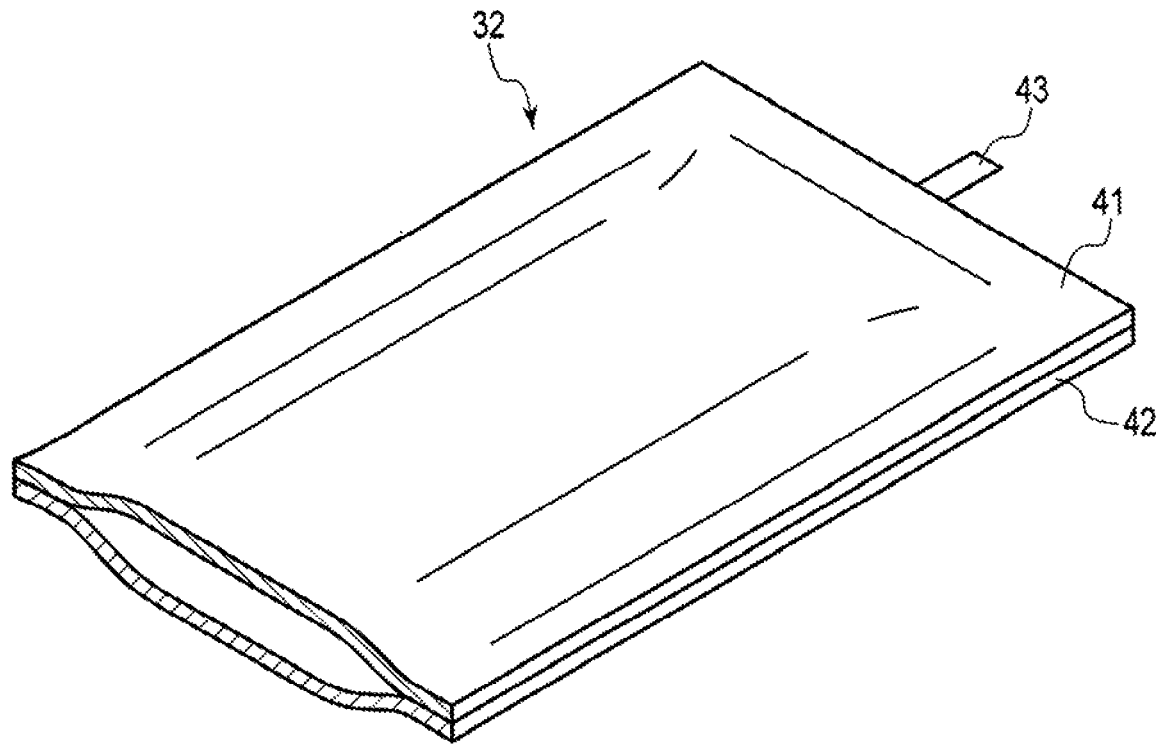
FIG. 3 is a partially cutaway perspective view showing a configuration of a bag-shaped structure used in the cuff.
Figure 4:
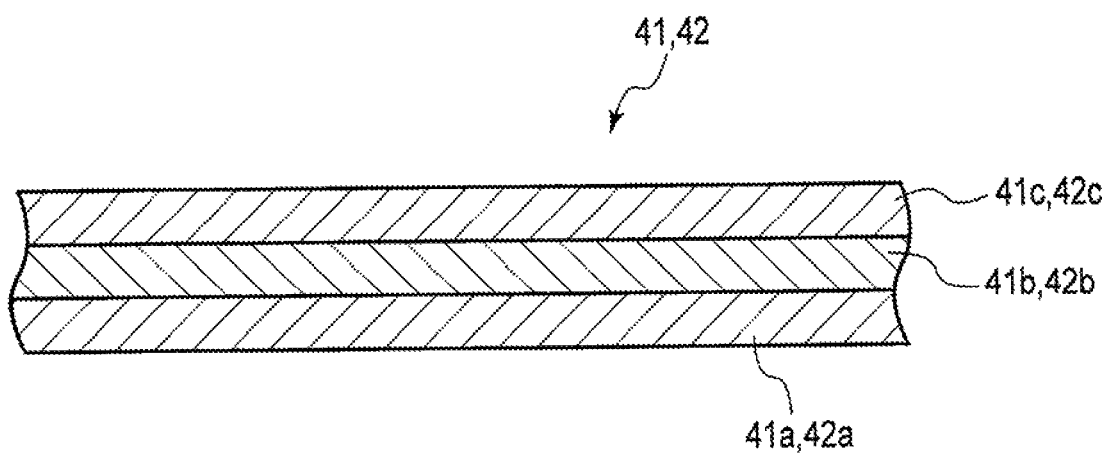
FIG. 4 is a cross-sectional view showing an example of a configuration of a sheet member used in the bag-shaped structure.

FIG. 1 is a perspective view showing a configuration of a blood pressure monitor 1 according to an embodiment of the present invention. FIG. 2 is a cross-sectional view showing a configuration of the cuff 12 used in the blood pressure monitor 1. FIG. 3 is a partially cutaway perspective view showing a configuration of the bag-shaped structure 32 used in the cuff 12. FIG. 4 is a cross-sectional view showing an example of a configuration of sheet members 41 and 42 forming the bag-shaped structure 32. FIGS. 5 and 6 are cross-sectional views showing a relationship between the cuff and a living body when the blood pressure monitor 1 is worn on the living body, at the time of deflation and inflation, respectively, of the bag-shaped structure.

The blood pressure monitor 1 is an electronic blood pressure monitor to be worn on, for example, the wrist. As shown in FIG. 1, the blood pressure monitor 1 includes an apparatus main body 11 and a cuff 12.

The apparatus main body 11 includes a case 21, a display unit 22, an operation unit 23, a pump 24, an on-off valve 25, a pressure sensor 26, a power supply unit 27, and a controller 28. The apparatus main body 11 further includes a flow path of air for fluidly connecting the pump 24, the on-off valve 25, the pressure sensor 26, and the cuff 12. For example, the air flow path is formed by arranging a tube or the like made of a resin material or the like in the case 21.

The case 21 includes a display unit 22 arranged on its upper surface. The case 21 houses the pump 24, the on-off valve 25, the pressure sensor 26, the power supply unit 27, and the controller 28. The case 21 is connected integrally with the cuff 12.

The display unit 22 is electrically connected to the controller 28. The display unit 22 is, for example, a liquid crystal display or an organic electroluminescence display. The display unit 112 displays various types of information, including measurements such as blood pressure values (e.g., systolic blood pressure and diastolic blood pressure) and a heart rate.

The operation unit 23 is configured in such a manner that a command from the user can be entered thereto. For example, the operation unit 23 is a button provided in the case 21 or a touch panel provided in the display unit. The operation unit 23 converts the command into an electric signal in response to an operation by the user. The operation unit 23 is electrically connected to the controller 28 and outputs an electric signal to the controller 28.

The pump 24 is, for example, a rolling pump. The pump 24 compresses air and supplies the compressed air to the cuff 12 via the flow path. The pump 24 is electrically connected to the controller 28.

The on-off valve 25 is an electromagnetic valve electrically connected to the controller 28. The on-off valve 25 is opened and closed in accordance with the command from the controller 28. By opening the on-off valve 25, the flow path and the atmosphere are made continuous, thus reducing the pressure in the flow path.

The pressure sensor 26 detects the pressure in the flow path. The pressure sensor 26 is electrically connected to the controller 28, converts the detected pressure into an electric signal, and outputs the electric signal to the controller 28. Here, since the flow path is continuous with a bag-shaped structure 32 (which will be described later) of the cuff 12, the pressure in the flow path equals the pressure in the internal space of the bag-shaped structure 32.

The power supply unit 27 is, for example, a secondary battery such as a lithium ion battery. The power supply unit 27 is electrically connected to the controller 28. The power supply unit 27 supplies power to the controller 28.

The controller 28 supplies power to the display unit 22, the operation unit 23, the pump 24, the on-off valve 25, and the pressure sensor 26. Moreover, the controller controls the operations of the display unit 22, the pump 24, and the on-off valve 25 on the basis of electric signal output from the operation unit 23 and the pressure sensor 26.

For example, when a command to measure a blood pressure is entered from the operation unit 23, the controller 28 drives the pump 24 and sends the compressed air to the cuff 12. Furthermore, the controller 28 controls whether to drive or stop the pump 24, and whether to open or close the on-off valve 25, on the basis of an electric signal output from the pressure sensor 26. Moreover, the controller 28 obtains measurements such as blood pressure values (e.g., systolic blood pressure and diastolic blood pressure) and a heart rate from the electric signal output by the pressure sensor 26, and outputs an image signal corresponding to the measurements to the display unit 22.

As shown in FIGS. 1 and 2, the cuff 12 includes a base material 31 and a bag-shaped structure 32. The cuff 12 is wrapped around the wrist, and is thus fixed to the wrist.

The base material 31 is set to be bent along the shape of the arm. The base material 31 is configured in such a manner, for example, that one end is formed integrally with the case 21, and the other end is fixable to the case 21 with a fastener or the like. The base material 31 supports the bag-shaped structure 32 on its inner surface. For example, the base material 31 includes, on its inner surface, a joint layer 31a, such as an adhesive or a double-sided tape, for joining the bag-shaped structure 32. The base material 31 is formed of a hard resin material.

As shown in FIGS. 2 and 3, the bag-shaped structure 32 is formed in a rectangular bag shape that is longer in one direction. The bag-shaped structure 32 forms an air chamber whose internal space is fluidly connected to the flow path of the apparatus main body 11. The bag-shaped structure 32 is arranged on the inner surface of the base material 31 so as to be bent along the inner surface of the base material 31. The width of the bag-shaped structure 32 is set to, for example, 40 mm or lower.

More specifically, as shown in FIGS. 2 and 3, the bag-shaped structure 32 includes a rectangular first sheet member 41, a second sheet member 42 having the same shape as the first sheet member 41, and a connection tube 43 which fluidly connects the internal space configured by the first sheet member 41 and the second sheet member 42 and the flow path of the apparatus main body 11.

The bag-shaped structure 32 is formed by joining peripheral portions of the first sheet member 41 and the second sheet member 42. The first sheet member 41 and the second sheet member 42 are joined by, for example, laser welding, high-frequency welding, hot press welding, or bonding with an adhesive or a double-sided tape.

The first sheet member 41 is a sheet-like member formed of a thermoplastic elastomer. Examples of the thermoplastic elastomer that can be used to form the first sheet member 41 include a thermoplastic polyurethane (hereinafter referred to as TPU) resin, a polyvinyl chloride (hereinafter referred to as PVC) resin, an ethylene-vinyl acetate (hereinafter referred to as EVA) resin, a thermoplastic polystyrene (hereinafter referred to as TPS) resin, a thermoplastic polyolefin (hereinafter referred to as TPO) resin, a thermoplastic polyester (hereinafter referred to as TPEE) resin, and a thermoplastic polyamide (hereinafter referred to as TPA) resin. As the thermoplastic elastomer, it is preferable to use TPU.

The first sheet member 41 is provided on the base material 31. The first sheet member 41 has a multilayer structure including a plurality of layers formed of a plurality of types of materials.

The first sheet member 41 is configured in, for example, a two-type, three-layer structure, in which at least two types of materials are stacked in three layers. As shown in FIG. 4, the first sheet member 41 includes a first layer 41a, a second layer 41b, and a third layer 41c. The first layer 41a forms an outer layer of the first sheet member 41 on the side of the second sheet member 42. The second layer 41b forms an inner layer of the first sheet member 41. The third layer 41c forms an outer layer of the first sheet member 41 on the side of the base material 31.

Preferably, the first sheet member 41 is configured in such a manner that the first layer 41a opposed to the second sheet member 42 is formed of a material having a higher Shore A hardness than the other layers. Here, the Shore A hardness refers to a durometer hardness obtained by a Type A durometer hardness test as specified in JIS K6253-3: 2012 ("Rubber, vulcanized or thermoplastic Determination of hardness—Part 3: Durometer hardness"). More preferably, the first sheet member 41 is configured in such a manner that the first layer 41a and the third layer 41c forming the outer layers of the first sheet member 41 are formed of a material having a higher Shore A hardness than the other layer forming the inner layer, namely, than the second layer 41b in the present embodiment. For example, the first layer 41a and the third layer 41c are formed of the same material.

As a specific example, for the first layer 41a and the third layer 41c, TPU having a Shore A hardness of 70 or higher is used as a thermoplastic elastomer. For the second layer 41b, TPU having a Shore A hardness of 65 or lower is used as a thermoplastic elastomer.

The first sheet member 41 is configured in such a manner that the first layer 41a and the third layer 41c forming the outer layers have the same thickness. In terms of thickness ratio, the first sheet member 41 has a layer composition ratio represented by $1:2:1 \leq T1:T2:T1 \leq 1:20:1$, where T1 represents the thickness of each of the outer layers and T2 represents the thickness of the inner layer. Preferably, the thickness ratio of the first sheet member 41 is set to be $1:4:1 \leq T1:T2:T1 \leq 1:10:1$. That is, $T1a:T2b:T1c$ is set between 1:2:1 and 1:20:1, preferably between 1:4:1 and 1:10:1, where T1a represents the thickness of the first layer 41a, T2b represents the thickness of the second layer 41b, and T1c represents the thickness of the third layer 41c.

The above-described first sheet member 41 is molded by, for example, T-die extrusion method or inflation method. The thickness of the first sheet member 41 is preferably in the range between 0.05 mm and 0.50 mm, and more preferably in the range between 0.10 mm and 0.40 mm. This is because, if the thickness of the bag-shaped structure 32 is too small, the risk of tearing or the like may be incurred, and if the thickness of the bag-shaped structure 32 is too large, the risk of reduction in shape conformability may be incurred when the bag-shaped structure 32 is inflated. The layer composition ratio of the first sheet member 41 is controlled by adjusting the discharge amount of the resin forming each layer at the time of molding.

The second sheet member 42 is a sheet-like member formed of a thermoplastic elastomer. Examples of the thermoplastic elastomer that can be used to form the first sheet member 41 include TPU, PVC, EVA, TPS, TPO, TPEE, and TPA, etc. As the thermoplastic elastomer, it is preferable to use TPU.

The second sheet member 42 is in contact with a living body when the cuff 12 is worn thereon. The second sheet member 42 has a multilayer structure including a plurality of layers formed of a plurality of types of materials.

The second sheet member 42 is configured in, for example, a two-type, three-layer structure, in which at least two types of materials are stacked in three layers. For example, the second sheet member 42 has the same configuration as the first sheet member 41. As shown in FIG. 4, the second sheet member 42 includes a first layer 42a, a second layer 42b, and a third layer 42c. The first layer 42a forms an outer layer of the second sheet member 42 on the side of the living body. The second layer 41b forms an inner layer of the second sheet member 42. The third layer 41c forms an outer layer of the second sheet member 42 on the side of the first sheet member 41.

Preferably, the second sheet member 42 is configured in such a manner that the first layer 41a opposed to the living body is formed of a material having a Shore A hardness higher than that of the other layers. More preferably, the second sheet member 42 is configured in such a manner that the first layer 42a and the third layer 42c, forming the outer layers of the second sheet member 42, are formed of a material having a higher Shore A hardness than the other layer forming the inner layer, namely, than the second layer 42b in the present embodiment. For example, the first layer 42a and the third layer 42c are formed of the same material.

As a specific example, for the first layer 42a and the third layer 42c, TPU having a Shore A hardness of 70 or higher is used as a thermoplastic elastomer. For the second layer 42b, TPU having a Shore A hardness of 65 or lower is used as a thermoplastic elastomer.

The second sheet member 42 is configured in such a manner that the first layer 41a and the third layer 41c forming the outer layers have the same thickness. In terms of thickness ratio, the second sheet member 42 has a layer composition ratio represented by $1:2:1 \leq T1:T2:T1 \leq 1:20:1$, where T1 represents the thickness of each of the outer layers, and T2 represents the thickness of the inner layer. Preferably, the thickness ratio of the second sheet member 42 is set to be $1:4:1 \leq T1:T2:T1 \leq 1:10:1$. That is, $T1a:T2b:T1c$ is set between 1:2:1 and 1:20:1, preferably between 1:4:1 and 1:10:1, where T1a represents the thickness of the first layer 42a, T2b represents the thickness of the second layer 42b, and T1c represents the thickness of the third layer 42c.

The above-described second sheet member 42 is molded by, for example, T-die extrusion method or inflation method. The thickness of the second sheet member 42 is preferably in the range between 0.05 mm and 0.50 mm, and more preferably in the range between 0.10 mm and 0.40 mm. If the thickness is too small, the risk of tearing, for example, may be incurred. If the thickness is too large, the shape conformability to a living body is reduced when the bag-shaped structure 32 is inflated, which may make the adhesion of the bag-shaped structure 32 to the living body insufficient, incurring the risk of reduction in compressibility. The layer composition ratio of the second sheet member 42 is controlled by adjusting the discharge amount of the resin forming each layer at the time of molding.

The connection tube 43 is formed of a resin material and has flexibility. The connection tube 43 is fixed to one end as viewed in the longitudinal direction of the bag-shaped structure 32. One end of the connection tube 43 is connected to the internal space of the bag-shaped structure 32, which is configured by the first sheet member 41 and the second sheet member 42. The connection tube 43 is connected to the flow path of the apparatus main body 11.

Next, measurement of the blood pressure value using the blood pressure monitor 1 will be described with reference to FIGS. 1, 5, and 6.

At the time of measuring the blood pressure value, the user wears the cuff 12 on a living body, e.g., on the wrist 100 in this embodiment. As a result, as shown in FIG. 5, the bag-shaped structure 32 of the cuff 12 comes into contact with the wrist 100. Next, the user operates the operation unit 23 shown in FIG. 1 and enters a command corresponding to the start of measurement of blood pressure values.

In response to the command entry operation, the operation unit 23 outputs an electric signal corresponding to the start of measurement to the controller 28. Upon receiving the electric signal, the controller 28 closes the on-off valve 25, drives the pump 24, and supplies compressed air to the bag-shaped structure 32 via the flow path. Thereby, the bag-shaped structure 32 starts to inflate.

The pressure sensor 26 detects the pressure in the internal space of the bag-shaped structure 32, and outputs an electric signal corresponding to the detected pressure to the controller 28. Based on the received electric signal, the controller 28 determines whether or not the pressure in the internal space of the bag-shaped structure 32 has reached a predetermined pressure for blood pressure measurement. When the pressure in the internal space of the bag-shaped structure 32 has reached the predetermined pressure, the controller 28 stops driving the pump 24. At this time, the bag-shaped structure 32 is sufficiently inflated, as shown in FIG. 6, and the inflated bag-shaped structure 32 presses the wrist and occludes the artery 110 in the wrist 100.

Thereafter, the controller 28 controls the on-off valve 25 to repeatedly open and close the on-off valve 25, or adjust the opening degree of the on-off valve 25 to reduce the pressure in the internal space of the bag-shaped structure 32. On the basis of the electric signal output by the pressure sensor 26 in the process of reducing the pressure, the controller 28 obtains measurements such as blood pressure values (e.g., systolic blood pressure and diastolic blood pressure) and a heart rate. The controller 28 outputs an image signal corresponding to the obtained measurements to the display unit 22.

Upon receiving the image signal, the display unit 22 displays the measurements on the screen. The user visually recognizes the display unit 22 to confirm the measurements. After the measurement is completed, the user unfastens the fastener and removes the blood pressure monitor 1 from the wrist.

With the above-described configuration, the cuff 12 used in the blood pressure monitor 1 according to the embodiment includes a bag-shaped structure 32 formed of a plurality of types of materials with different levels of Shore A hardness, and formed of multi-layer sheet members and 42 configured in such a manner that the Shore A hardness of the outer layers is higher than the Shore A hardness of the inner layer. The bag-shaped structure 32 is configured in such a manner that the layer composition ratio T1:T2:T1 of the outer layers and the inner layer of the multi-layer sheet members 41 and 42 ranges from 1:2:1 to 1:20:1, in terms of thickness ratio. In addition, the physical properties of the outer layers having a high Shore A hardness and the physical properties of the inner layer having a low Shore A hardness make a contribution. As a result, the bag-shaped structure 32 with the above-described configuration is excellent in creep resistance and vascular compressibility. Since the bag-shaped structure 32 can be formed merely by joining the first sheet member 41 and the second sheet member 42, the processing cost can be reduced.

That is, since the cuff 12 is required to have high adhesion to the human skin surface and good vascular compressibility when inflated with air, it is preferable that the material of the bag-shaped structure 32 used for the cuff 12 has high flexibility. Under the circumstances, elastomeric materials have been frequently used for the bag-shaped structure in the past. A plasticizer is often added to elastic materials to impart softness; however, a plasticizer carries the risk of "bleed-out", namely, the plasticizer may bleed out over time under the usage environment. When the plasticizer bleed-out occurs in the elastomeric material, the elastomeric material is cured, resulting in reduction in vascular compressibility. There is also a risk for development of a rash, for example, on the human skin in contact therewith.

On the other hand, an elastomeric material not containing a plasticizer is free from the above-mentioned risk; however, it has been found that such an elastic material has a high ratio of low-molecular components, exhibits adhesiveness, and sticks to the human skin when worn on a living body. This adhesiveness inhibits the smoothness on the human skin surface and decreases the vascular compressibility. In addition, the tactile sensation to the human body is remarkably reduced.

In addition, an elastomeric material having high flexibility may be slackened by creep when inflated and deflated repeatedly. Such slack causes a pressure loss at the time of compression, and inhibits vascular compressibility.

In the bag-shaped structure 32 of the cuff 12 according to the present embodiment, a flexible thermoplastic elastomer having a Shore A hardness of 65 or lower and formed of TPU is used for the second layers 41b and 42b, which form the inner layers of the first sheet member 41 and the second sheet member 42. In the bag-shaped structure 32, a rigid thermoplastic elastomer having a Shore A hardness of 70 or higher and formed of TPU is used for the first layers 41a and 42a and the third layers 41c and 42c, which form the outer layers of the first sheet member 41 and the second sheet member 42. Thereby, the first sheet member 41 and the second sheet member 42 have a multilayer structure, in which a layer formed of a flexible material is covered with layers formed of a rigid material.

With the above-described bag-shaped structure 32, it is possible to obtain high vascular compressibility by virtue of the second layers 41b and 42b, and to obtain high creep resistance by virtue of the first layers 41a and 42a and the third layers 41c and 42c. In addition, since the first layer 41a and the third layer 42c, which form the opposed surfaces of the first sheet member 41 and the second sheet member 42, respectively, and the first layer 42a of the second sheet member 42, which is brought into contact with a living body, are formed of a rigid material, the first sheet member 41 and the second sheet member 42 do not exhibit adhesiveness, resulting in improved smoothness. As a result, when the bag-shaped structure 32 is inflated, it is possible to prevent the inflation from being inhibited by adhesion between the first sheet member 41 and the second sheet member 42, and to prevent the second sheet member 42 from adhering to the human skin, resulting in prevention of reduction in vascular compressibility.

[Modifications]

Figure 10:
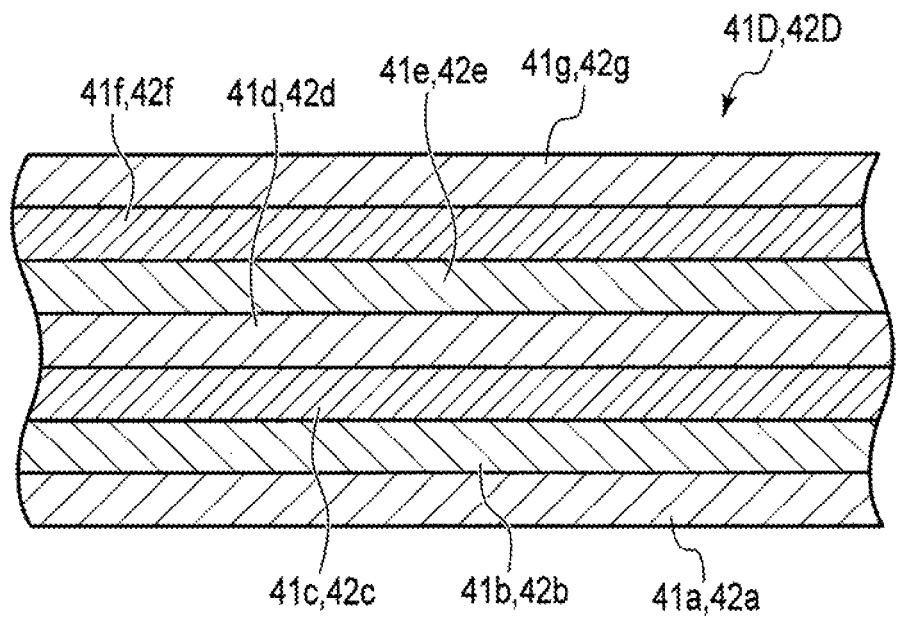
FIG. 10 is a cross-sectional view showing a configuration of a first sheet member and a second sheet member of a bag-shaped structure according to a fourth modification.
Figure 11:
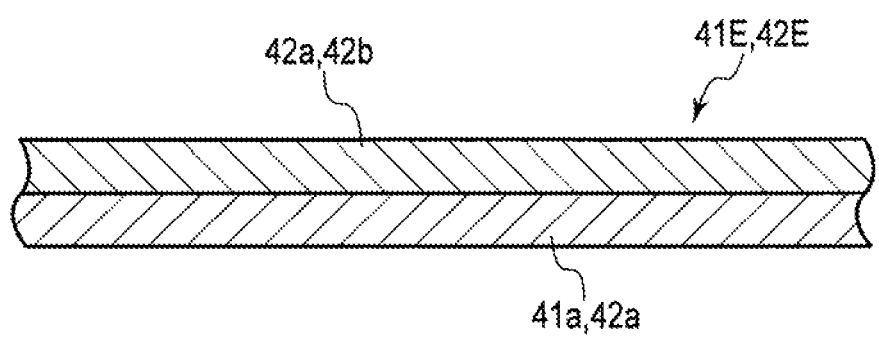
FIG. 11 is a cross-sectional view showing a configuration of a first sheet member of a bag-shaped structure according to a fifth modification.

Next, modifications of the first sheet member 41 and the second sheet member 42 used for the bag-shaped structure 32 will be described with reference to FIGS. 7 to 11. FIG. 7 is a cross-sectional view showing a configuration of a first sheet member 41A and a second sheet member 42A of a bag-shaped structure 32 according to a first modification; FIG. 8 is a cross-sectional view showing a configuration of a first sheet member 41B and a second sheet member 42B of a bag-shaped structure 32 according to a second modification; FIG. 9 is a cross-sectional view showing a configuration of a first sheet member 41C and a second sheet member 42C of a bag-shaped structure 32 according to a third modification; FIG. 10 is a cross-sectional view showing a configuration of a first sheet member 41D and a second sheet member 42D of a bag-shaped structure 32 according to a fourth modification; and FIG. 11 is a cross-sectional view showing a configuration of a first sheet member 41E of a bag-shaped structure 32 according to a fifth modification.

[First Modification]

As shown in FIG. 7, the first sheet member 41A and the second sheet member 42A of the bag-shaped structure 32 according to the first modification are configured in a two-type, five-layer structure, in which two types of materials are stacked in five layers. The first sheet member 41A and the second sheet member 42A are sheet-like members formed of a thermoplastic elastomer. For the thermoplastic elastomer, a material similar to that of the first sheet member 41 and the second sheet member 42 described above may be used.

As shown in FIG. 7, the first sheet member 41A includes a first layer 41a, a second layer 41b, a third layer 41c, a fourth layer 41d, and a fifth layer 41e. The first layer 41a forms an outer layer of the first sheet member 41A on the side of the second sheet member 42A. The second layer 41b, the third layer 41c, and the fourth layer 41d form inner layers of the first sheet member 41A. The fifth layer 41e forms an outer layer of the first sheet member 41A on the side of the base material 31.

The first sheet member 41A is configured in such a manner that the first layer 41a, the third layer 41c, and the fifth layer 41e are formed of a material having a Shore A hardness higher than that of the second layer 41b and the fourth layer 41d. For example, the first layer 41a, the third layer 41c, and the fifth layer 41e are formed of the same material, and the second layer 41b and the fourth layer 41d are formed of the same material.

As a specific example, for the first layer 41a and the third layer 41c, TPU having a Shore A hardness of 70 or higher is used as a thermoplastic elastomer. For the second layer 41b, TPU having a Shore A hardness of 65 or lower is used as a thermoplastic elastomer.

In terms of thickness ratio, the first sheet member 41A has a layer composition ratio represented by $1:2:1 \leq T1:T2:T1 \leq 1:20:1$, where T1 represents the thickness of each of the outer layers, and T2 represents the thickness of the inner layers. Preferably, the thickness ratio of the first sheet member 41A is set to be $1:4:1 \leq T1:T2:T1 \leq 1:10:1$. That is, $T1a:T2b:T1c$ is set between 1:2:1 and 1:20:1, preferably between 1:4:1 and 1:10:1, where $T1a$ represents the thickness of the first layer 41a; $T2b$ represents the total thickness of the second layer 41b, the third layer 41c, and the fourth layer 41d; and $T1c$ represents the thickness of the fifth layer 41e.

The first sheet member 41A may have a three-type, five-layer structure, a four-type, five-layer structure, or a five-type, five-layer structure. That is, the first sheet member 41A can be suitably configured, if at least the first layer 41a opposed to the second sheet member 42A is formed of a material having a Shore A hardness that does not provide adhesiveness. In the case of TPU, for example, the Shore A hardness that does not provide adhesiveness is typically 60 or lower.

The first sheet member 41A is molded by, for example, T-die extrusion method or inflation method. Preferably, the thickness of the first sheet member 41A is in the range between 0.05 mm and 0.50 mm, and more preferably in the range between 0.10 mm and 0.40 mm.

The second sheet member 42A includes a first layer 42a, a second layer 42b, a third layer 42c, a fourth layer 42d, and a fifth layer 42e, and has a two-type, five-layer structure, as in the first sheet member 41A, and has a layer composition ratio which is the same as that of the first sheet member 41A. Therefore, a detailed configuration of the second sheet member 42A will be omitted. The first layer 42a forms an outer layer of the second sheet member 42 on the side of the living body. The fifth layer 41e forms an outer layer of the second sheet member 42A on the side of the first sheet member 41A. The second sheet member 42A can be suitably configured, if the first layer 42a opposed to a living body and the fifth layer 41e opposed to the first sheet member 41A are formed of a material having a Shore A hardness that does not provide adhesiveness.

The bag-shaped structure 32 including the first sheet member 41A and the second sheet member 42A with the above-described configuration produce the same effect as that of the bag-shaped structure 32 including the first sheet member 41 and the second sheet member 42 according to the above-described embodiment.

[Second Modification]

As shown in FIG. 8, the first sheet member 41B and the second sheet member 42B of the bag-shaped structure 32 according to the second modification are configured in a three-type, three-layer structure, in which three types of materials are stacked in three layers. The first sheet member 41B and the second sheet member 42B are sheet-like members formed of a thermoplastic elastomer. For the thermoplastic elastomer, a material similar to that of the first sheet member 41 and the second sheet member 42 described above may be used.

As shown in FIG. 8, the first sheet member 41B and the second sheet member 42B include first layers 41a and 42a, second layers 41b and 41b, and third layers 41c and 41c. The first layer 41a of the first sheet member 41B forms an outer layer of the first sheet member 41B on the side of the second sheet member 42B, and the first layer 41a of the second sheet member 42B forms an outer layer of the second sheet member 42C on the side of the living body. The first sheet member 41B and the second sheet member 42B are configured in such a manner that the outer layer opposed to the living body, or the other one of the first sheet member 41B and the second sheet member 42B, has a hardness that does not provide adhesiveness.

The first sheet member 41B and the second sheet member 42B are configured in such a manner that the first layers 41a and 42a and the third layers 41c and 42c are formed of a material having a Shore A hardness higher than that of the second layer 41b and 42b. The first layers 41a and 42a and the third layers 41c and 42c are formed of different materials.

As a specific example, TPU that exhibits a Shore A hardness of 70 or higher is used as a thermoplastic elastomer for the first layers 41a and 42a. For the second layers 41b and 42b, TPU having a Shore A hardness of 65 or lower is used as a thermoplastic elastomer. For the third layers 41c and 42c, TPU having a Shore A hardness of 70 or higher and having a composition different from that of the first layers 41a and 42a is used as a thermoplastic elastomer.

In terms of thickness ratio, the first sheet member 41B and the second sheet member 42B have a layer composition ratio represented by $1:2:1 \leq T1:T2:T1 \leq 1:20:1$, where T1 represents the thickness of each of the outer layers, and T2 represents the thickness of the inner layer. Preferably, the thickness ratio of the first sheet member 41B is set to be $1:4:1 \leq T1:T2:T1 \leq 1:10:1$. That is, $T1a:T2b:T1c$ is set between 1:2:1 and 1:20:1, preferably between 1:4:1 and 1:10:1, where $T1a$ represents the thickness of the first layer 41a, $T2b$ represents the thickness of the second layer 41b, and $T1c$ represents the thickness of the third layer 41c.

The first sheet member 41B and the second sheet member 42B are molded by, for example, T-die extrusion method or inflation method. Preferably, the thickness of the first sheet member 41B and the second sheet member 42B is in the range between 0.05 mm and 0.50 mm, and more preferably in the range between 0.10 mm and 0.40 mm.

The bag-shaped structure 32 including the first sheet member 41B and the second sheet member 42B with the above-described configuration produces the same effect as that of the bag-shaped structure 32, including the first sheet member 41 and the second sheet member 42, according to the above-described embodiment.

[Third Modification]

As shown in FIG. 9, the first sheet member 41C and the second sheet member 42C of the bag-shaped structure 32 according to the third modification are configured in a three-type, four-layer structure, in which three types of materials are stacked in three layers. The first sheet member 41C and the second sheet member 42C are sheet-like members formed of a thermoplastic elastomer. For the thermoplastic elastomer, a material similar to that of the first sheet member 41 and the second sheet member 42 described above may be used.

As shown in FIG. 9, the first sheet member 41C and the second sheet member 42C include first layers 41a and 42a, second layers 41b and 41b, third layers 41c and 41c, and fourth layers 41d and 42d. The first layer 41a of the first sheet member 41C forms an outer layer of the first sheet member 41C on the side of the second sheet member 42C, and the first layer 41a of the second sheet member 42C forms an outer layer of the second sheet member 42C on the side of the living body. The second layers 41b and 42b and the third layers 41c and 42c of the first sheet member 41C and the second sheet member 42C form the inner layers of the first sheet member 41C and the second sheet member 42C. The fourth layer 41d of the first sheet member 41C form an outer layer of the first sheet member 41C on the side of the base material 31, and the fourth layer 42d of the second sheet member 42C forms an outer layer of the second sheet member 42C on the side of the first sheet member 41C.

The first sheet member 41C and the second sheet member 42C are configured in such a manner that the outer layer opposed to the living body or the other one of the first sheet member 41C and the second sheet member 42C has a hardness that does not provide adhesiveness.

The first sheet member 41C and the second sheet member 42C are configured in such a manner that the first layers 41a and 42a, the third layers 41c and 42c, and the fourth layers 41d and 42d are formed of a material having a Shore A hardness higher than that of the second layers 41b and 42b. Also, the first layers 41a and 42a and the fourth layers 41d and 42d are formed of the same material, and the first layers 41a and 42a, the second layers 41b and 42b, and the third layers 41c and 42c are formed of different materials.

As a specific example, for the first layers 41a and 42a and the fourth layers 41d and 42d, TPU having a Shore A hardness of 70 or higher is used as a thermoplastic elastomer. For the second layers 41b and 42b, TPU having a Shore A hardness of 65 or lower is used as a thermoplastic elastomer. For the third layers 41c and 42c, TPU having a Shore A hardness of 70 or higher, and having a composition different from that of the first layers 41a and 42a and the fourth layers 41d and 42d, is used as a thermoplastic elastomer. The third layers 41c and 42c are provided to adjust, for example, the flexibility of the first sheet member 41C and the second sheet member 42C.

In terms of thickness ratio, the first sheet member 41C has a layer composition ratio represented by 1:2:1≤T1:T2:T1≤1:20:1, where T1 represents the thickness of each of the outer layers, and T2 represents the thickness of the inner layers. Preferably, the thickness ratio of the first sheet member 41 is set to be 1:4:1≤T1:T2:T1≤1:10:1. That is, T1a:T2b:T1c is set between 1:2:1 and 1:20:1, preferably between 1:4:1 and 1:10:1, where T1a represents the thickness of the first layer 41a, T2b represents the total thickness of the second layer 41b and the third layer 41c, and T1c represents the thickness of the fourth layer 41d.

The first sheet member 41C and the second sheet member 42C are molded by, for example, T-die extrusion method or inflation method. Preferably, the thickness of the first sheet member 41C and the second sheet member 42C is in the range between 0.05 mm and 0.50 mm, and more preferably in the range between 0.10 mm and 0.40 mm.

The bag-shaped structure 32 including the first sheet member 41C and the second sheet member 42C with the above-described configuration produces the same effect as that of the bag-shaped structure 32 including the first sheet member 41 and the second sheet member 42 according to the above-described embodiment.

[Fourth Modification Example]

As shown in FIG. 10, the first sheet member 41D and the second sheet member 42D of the bag-shaped structure 32 according to the fourth modification are configured in a three-kind, seven-layer structure, in which three kinds of materials are stacked in seven layers. The first sheet member 41D and the second sheet member 42D are sheet-like members formed of a thermoplastic elastomer. For the thermoplastic elastomer, a material similar to that of the first sheet member 41 and the second sheet member 42 described above may be used.

As shown in FIG. 10, the first sheet member 41D and the second sheet member 42D include first layers 41a and 42a, second layers 41b and 41b, third layers 41c and 41c, fourth layers 41d and 42d, fifth layers 41e and 42e, sixth layers 41f and 42f, and seventh layers 41g and 42g. The first layer 41a of the first sheet member 41D forms an outer layer of the first sheet member 41D on the side of the second sheet member 42D, and the first layer 41a of the second sheet member 42D forms an outer layer of the second sheet member 42D on the side of the living body. The second layers 41b and 42b to the sixth layers 41f and 42f of the first sheet member 41D, and the second sheet member 42D, form the inner layers of the first sheet member 41D and the second sheet member 42D. The seventh layer 41g of the first sheet member 41D forms an outer layer of the first sheet member 41D on the side of the base material 31, and the seventh layer 42g of the second sheet member 42D forms an outer layer of the second sheet member 42D on the side of the first sheet member 41D.

The first sheet member 41D and the second sheet member 42D are configured in such a manner that the outer layer opposed to the living body or the other one of the first sheet member 41D and the second sheet member 42D has a hardness that does not provide adhesiveness.

The first sheet member 41D and the second sheet member 42D are configured in such a manner that the first layers 41a and 42a, the third layers 41c and 42c, the fourth layers 41d and 42d, the sixth layers 41f and 42f, and the seventh layers 41g and 42g are formed of a material having a Shore A hardness higher than that of the second layers 41b and 42b and the fifth layers 41e and 42e. The first layers 41a and 42a, the fourth layers 41d and 42d, and the seventh layers 41g and 42g are formed of the same material, and the third layers 41c and 42c and the sixth layers 41f and 42f are formed of the same material. The first layers 41a and 42a, the fourth layers 41d and 42d, and the seventh layers 41g and 42g are formed of a material different from a material of the third layers 41c and 42c and the sixth layers 41f and 42f.

As a specific example, for the first layers 41a and 42a, the fourth layers 41d and 42d, and the seventh layers 41g and 42g, TPU having a Shore A hardness of 70 or higher is used as a thermoplastic elastomer. For the second layers 41b and 42b and the fifth layers 41e and 42e, TPU having a Shore A hardness of 65 or lower is used as a thermoplastic elastomer. For the third layer 41c and 42c and the sixth layers 41f and 42, TPU having a Shore A hardness of 70 or higher and having a composition different from that of the first layers 41a and 42a and the fourth layers 41d and 42d is used as a thermoplastic elastomer. The third layers 41c and 42c and the sixth layers 41f and 42, for example, are provided to adjust the flexibility of the first sheet member 41D and the second sheet member 42D.

In terms of thickness ratio, the first sheet member 41D has a layer composition ratio represented by 1:2:1≤T1:T2:T1≤1:20:1, where T1 represents the thickness of each of the outer layers and T2 represents the thickness of the inner layers. Preferably, the thickness ratio of the first sheet member 41 is set to be 1:4:1≤T1:T2:T1≤1:10:1. That is, T1a:T2b:T1c is set between 1:2:1 and 1:20:1, preferably between 1:4:1 and 1:10:1, where T1a represents the thickness of the first layer 41a, T2b represents the total thickness of the second layer 41b, the third layer 41c, the fourth layer 41d, the fifth layer 41e, and the sixth layer 41f, and T1c represents the thickness of the seventh layer 41g.

The first sheet member 41D and the second sheet member 42D are molded by, for example, T-die extrusion method or inflation method. Preferably, the thickness of the first sheet member 41D and the second sheet member 42D is in the range between 0.05 mm and 0.50 mm, and more preferably in the range between 0.10 mm and 0.40 mm.

The bag-shaped structure 32 including the first sheet member 41D and the second sheet member 42D with the above-described configuration produces the same effect as that of the bag-shaped structure 32, including the first sheet member 41 and the second sheet member 42, according to the above-described embodiment.

[Fifth Modification]

As shown in FIG. 11, the first sheet member 41E of the bag-shaped structure 32 according to the fifth modification has a two-type, two-layer structure, in which two types of materials are stacked in two layers, and the second sheet member 42E has the same configuration as the second sheet member 42 of the bag-shaped structure 32 according to the above-described embodiment. The first sheet member 41E is a sheet-like member formed of a thermoplastic elastomer. For the thermoplastic elastomer, a material similar to that of the first sheet member 41 described above may be used.

As shown in FIG. 11, the first sheet member 41E includes a first layer 41a and a second layer 41b. The first layer 41a of the first sheet member 41E forms an outer layer of the first sheet member 41E on the side of the second sheet member 42, and the second layer 41b forms an outer layer of the first sheet member 41E on the side of the base material 31.

The first sheet member 41E is configured in such a manner that the outer layer opposed to the second sheet member 42 has a hardness that does not provide adhesiveness. The first sheet member 41E is configured in such a manner that the first layer 41a is formed of a material having a Shore A hardness higher than that of the second layer 41b.

As a specific example, for the first layer 41a, TPU having a Shore A hardness of 70 or higher is used as a thermoplastic elastomer. For the second layer 41b, TPU having a Shore A hardness of 65 or lower is used as a thermoplastic elastomer.

The first sheet member 41E is molded by, for example, T-die extrusion method or inflation method. Preferably, the thickness of the first sheet member 41E is in the range between 0.05 mm and 0.50 mm, and more preferably in the range between 0.10 mm and 0.40 mm.

The bag-shaped structure 32 including the first sheet member 41E and the second sheet member 42 with the above-described configuration produces the same effect as that of the bag-shaped structure 32 including the first sheet member 41 and the second sheet member 42 according to the above-described embodiment. The outer layer of the first sheet member 41E on the side of the base material 31 has adhesiveness; however, it is joined to the inner surface of the base material 31 via the joint layer 31a, and there is thus no effect on the function on the bag-shaped structure 32.

The present invention is not limited to the above-described embodiment and its modifications. For example, the bag-shaped structure 32 is not limited to the above-described configuration, if the outer layer in contact with the living body and the outer layer exposed to the air chamber have a Shore A hardness that does not provide adhesiveness, and the advantageous effect of the present invention is achieved. That is, the bag-shaped structure 32 may be configured by suitably combining the sheet members with the configurations of the above-described embodiment and its modifications.

In the above-described embodiment and its modifications, the first sheet member 41 and the second sheet member 42 are described as including a plurality of layers, such as the first layer, the second layer, and the third layer from the side of the living body 100 toward the base material 31, for the sake of simplicity; however, the number of the layers is not limited thereto. For example, the first sheet member 41 and the second sheet member 42 may be configured in such a manner that a first layer and a second layer form the outer layers, and a third layer forms the inner layer, if the first sheet member 41 and the second sheet member 42 are configured according to the above-described embodiment and its modifications.

The present invention is not limited to the above-described embodiment and can be modified in various manners in practice without departing from the gist of the invention. Moreover, the embodiments can be suitably combined where possible; in that case, the combined advantages are obtained. Furthermore, the above-described embodiment includes various stages of the invention, and various inventions can be extracted by suitably combining the structural elements disclosed herein. For example, if the object of the invention is achieved and the advantages of the invention are attained even after some of the structural elements are deleted from all the structural elements disclosed in the embodiment, the structure made up of the resultant structural elements can be extracted as an invention.

EXAMPLES

In order to make the features of the present invention more concrete, examples and evaluation tests will be described below. However, the scope of the present invention is not limited to the following examples.

Example 1

A bag-shaped structure 32 was formed of a first sheet member 41 and a second sheet member 42 having a two-type, three-layer structure. For first layers 41a and 42a and third layers 41c and 42c of the first sheet member 41, and the second sheet member 42, TPU having a Shore A hardness of 70 was used as a thermoplastic elastomer. For second layers 41b and 42b of the first sheet member 41 and the second sheet member 42, TPU having a Shore A hardness of 65 was used as a thermoplastic elastomer. The first sheet member 41 had a thickness of 0.15 mm. The second sheet member 42 had a thickness of 0.15 mm. The first sheet member 41 and the second sheet member 42 had a layer composition ratio represented by T1:T2:T1=1:8:1.

Example 2

A bag-shaped structure 32 was formed of a first sheet member 41 and a second sheet member 42 having a two-type, three-layer structure. For first layers 41a and 42a and third layers 41c and 42c of the first sheet member 41 and the second sheet member 42, TPU having a Shore A hardness of 95 was used as a thermoplastic elastomer. For second layers 41b and 42b of the first sheet member 41 and the second sheet member 42, TPU having a Shore A hardness of 60 was used as a thermoplastic elastomer. The first sheet member 41 had a thickness of 0.15 mm. The second sheet member 42 had a thickness of 0.15 mm. The first sheet member 41 and the second sheet member 42 had a layer composition ratio represented by T1:T2:T1=1:8:1.

Example 3

A bag-shaped structure 32 was formed of a first sheet member 41B and a second sheet member 42B having a three-type, three-layer structure. For first layers 41a and 42a of the first sheet member 41B and the second sheet member 42B, TPU having a Shore A hardness of 95 was used as a thermoplastic elastomer. For second layers 41b and 42b of the first sheet member 41B and the second sheet member 42B, TPU having a Shore A hardness of 65 was used as a thermoplastic elastomer. For third layers 41c and 42c of the first sheet member 41B and the second sheet member 42B, TPU having a Shore A hardness of 75 was used as a thermoplastic elastomer.

The first sheet member 41B had a thickness of 0.15 mm. The second sheet member 42B had a thickness of 0.15 mm. The first sheet member 41 and the second sheet member 42 had a layer composition ratio represented by T1:T2:T1=1:8:1.

Example 4

The bag-shaped structure 32 was formed of a first sheet member 41A and a second sheet member 42A having a two-type, five-layer structure. For first layers 41a and 42a, third layers 41c and 42c, and fifth layers 41e and 42e of the first sheet member 41A and the second sheet member 42A, TPU having a Shore A hardness of 95 was used as a thermoplastic elastomer. For second layers 41b and 42b and fourth layers 41d and 42d of the first sheet member 41A and the second sheet member 42A, TPU having a Shore A hardness of 65 was used as a thermoplastic elastomer.

The first sheet member 41A had a thickness of 0.15 mm. The second sheet member 42A had a thickness of 0.15 mm. The first sheet member 41 and the second sheet member 42 had a layer composition ratio represented by T1:T2:T1=1:8:1.

Example 5

A bag-shaped structure 32 was formed of a first sheet member 41 and a second sheet member 42 having a two-type, three-layer structure. For first layers 41a and 42a and third layers 41c and 42c of the first sheet member 41 and the second sheet member 42, TPU having a Shore A hardness of 95 was used as a thermoplastic elastomer. For second layers 41b and 42b of the first sheet member 41 and the second sheet member 42, TPU having a Shore A hardness of 60 was used as a thermoplastic elastomer. The first sheet member 41 had a thickness of 0.15 mm. The second sheet member 42 had a thickness of 0.15 mm. The first sheet member 41 and the second sheet member 42 had a layer composition ratio represented by T1:T2:T1=1:2:1. That is, the bag-shaped structure 32 of Example 5 was configured in such a manner that the first sheet member 41 and the second sheet member 42 had a layer composition ratio different from that of the bag-shaped structure 32 of Example 2.

Example 6

A bag-shaped structure 32 was formed of a first sheet member 41 and a second sheet member 42 having a two-type, three-layer structure. For first layers 41a and 42a and third layers 41c and 42c of the first sheet member 41 and the second sheet member 42, TPU having a Shore A hardness of 95 was used as a thermoplastic elastomer. For second layers 41b and 42b of the first sheet member 41 and the second sheet member 42, TPU having a Shore A hardness of 60 was used as a thermoplastic elastomer. The first sheet member 41 had a thickness of 0.15 mm. The second sheet member 42 had a thickness of 0.15 mm. The first sheet member 41 and the second sheet member 42 had a layer composition ratio represented by T1:T2:T1=1:4:1. That is, the bag-shaped structure 32 of Example 6 was configured in such a manner that the first sheet member 41 and the second sheet member 42 had a layer composition ratio different from that of the bag-shaped structure 32 of Example 2.

Example 7

A bag-shaped structure 32 was formed of a first sheet member 41 and a second sheet member 42 having a two-type, three-layer structure. For first layers 41a and 42a and third layers 41c and 42c of the first sheet member 41 and the second sheet member 42, TPU having a Shore A hardness of 95 was used as a thermoplastic elastomer. For second layers 41b and 42b of the first sheet member 41 and the second sheet member 42, TPU having a Shore A hardness of 60 was used as a thermoplastic elastomer. The first sheet member 41 had a thickness of 0.15 mm. The second sheet member 42 had a thickness of 0.15 mm. The first sheet member 41 and the second sheet member 42 had a layer composition ratio represented by T1:T2:T1=1:10:1. That is, the bag-shaped structure 32 of Example 7 was configured in such a manner that the first sheet member 41 and the second sheet member 42 had a layer composition ratio different from that of the bag-shaped structure 32 of Example 2.

Example 8

A bag-shaped structure 32 was formed of a first sheet member 41 and a second sheet member 42 having a two-type, three-layer structure. For first layers 41a and 42a and third layers 41c and 42c of the first sheet member 41 and the second sheet member 42, TPU having a Shore A hardness of 95 was used as a thermoplastic elastomer. For second layers 41b and 42b of the first sheet member 41 and the second sheet member 42, TPU having a Shore A hardness of 60 was used as a thermoplastic elastomer. The first sheet member 41 had a thickness of 0.15 mm. The second sheet member 42 had a thickness of 0.15 mm. The first sheet member 41 and the second sheet member 42 had a layer composition ratio represented by T1:T2:T1=1:20:1. That is, the bag-shaped structure 32 of Example 8 was configured in such a manner that the first sheet member 41 and the second sheet member 42 had a layer composition ratio different from that of the bag-shaped structure 32 of Example 2.

Comparative Example 1

For Comparative Example 1 to be compared with Examples 1 to 4, a bag-shaped structure was formed of a first sheet member and a second sheet member each having a single-layer structure. The first sheet member and the second sheet member had a Shore A hardness of 65, and the first sheet member 41A had a thickness of 0.15 mm.

Comparative Example 2

For Comparative Example 2 to be compared with Examples 1 to 4, a bag-shaped structure was formed of a first sheet member and a second sheet member each having a single-layer structure. The first sheet member and the second sheet member had a Shore A hardness of 70, and the first sheet member 41A had a thickness of 0.15 mm.

Comparative Example 3

For Comparative Example 3 to be compared with Examples 1 to 4, a bag-shaped structure was formed of a first sheet member and a second sheet member each having a two-type, three-layer structure. The first sheet member and the second sheet member of Comparative Example 3 are set in such a manner that the outer layer has a Shore A hardness lower than a Shore A hardness of the inner layer. Specifically, for first layers 41a and 42a and third layers 41c and 42c of the first sheet member and the second sheet member, TPU having a Shore A hardness of 65 was used as a thermoplastic elastomer. For second layers 41b and 42b of the first sheet member and the second sheet member, TPU having a Shore A hardness of 70 was used as a thermoplastic elastomer. The first sheet member 41A had a thickness of 0.15 mm. The second sheet member 42A had a thickness of 0.15 mm. The first sheet member and the second sheet member had a layer composition ratio represented by T1:T2:T1=1:25:1.

Comparative Example 4

For Comparative Example 4 to be compared with Examples 2 and 5 to 8, a bag-shaped structure was formed of a first sheet member and a second sheet member each having a two-type, three-layer structure. For first layers 41a and 42a and third layers 41c and 42c of the first sheet member and the second sheet member, TPU having a Shore A hardness of 95 was used as a thermoplastic elastomer. For second layers 41b and 42b of the first sheet member and the second sheet member, TPU having a Shore A hardness of 60 was used as a thermoplastic elastomer. The first sheet member had a thickness of 0.15 mm. The second sheet member had a thickness of 0.15 mm. The first sheet member and the second sheet member had a layer composition ratio represented by T1:T2:T1=1:1:1. That is, the bag-shaped structure of Comparative Example 4 was configured in such a manner that the first sheet member and the second sheet member had a layer composition ratio different from that of the bag-shaped structure 32 of Example 2.

Comparative Example 5

For Comparative Example 4 to be compared with Examples 2 and 5 to 8, a bag-shaped structure was formed of a first sheet member and a second sheet member each having a two-type, three-layer structure. For first layers 41a and 42a and third layers 41c and 42c of the first sheet member and the second sheet member, TPU having a Shore A hardness of 95 was used as a thermoplastic elastomer. For second layers 41b and 42b of the first sheet member and the second sheet member, TPU having a Shore A hardness of 60 was used as a thermoplastic elastomer. The first sheet member had a thickness of 0.15 mm. The second sheet member had a thickness of 0.15 mm. The first sheet member and the second sheet member had a layer composition ratio represented by T1:T2:T1=1:25:1. That is, the bag-shaped structure of Comparative Example 5 was configured in such a manner that the first sheet member 41 and the second sheet member 42 had a layer composition ratio different from that of the bag-shaped structure 32 of Example 2.

[Evaluation Test 1]

For Evaluation Test 1, a tactile sensation evaluation test was performed for the bag-shaped structures 32 according to Examples 1 to 7 and Comparative Examples 1 to 5.

In the tactile sensation evaluation test, each of the bag-shaped structure 32 produced in Examples 1 to 7 and Comparative Examples 1 to 5 was attached to a cuff 12 of a blood pressure monitor 1, and the blood pressure monitor 1 was used for discretionarily selected 10 people, with the cuff 12 of the blood pressure monitor 1 worn thereon. At this time, a tactile sensation drawing a response of having adhesiveness and surface roughness without smoothness was given "×", a tactile sensation drawing a response of having good smoothness and being comfortable to wear was given "o", and the bag-shaped structure 32 was determined as "good" if the ten respondents out of ten gave "o", and was otherwise determined as "not good".

[Evaluation Test 2]

For Evaluation Test 2, a vascular compressibility evaluation test was performed for the bag-shaped structures 32 according to Examples 1 to 7 and Comparative Examples 1 to 5.

In the vascular compressibility evaluation test, an upper-arm blood pressure monitor and a blood pressure monitor 1, to which each of the bag-shaped structures 32 produced in Examples 1 to 7 and Comparative Examples 1 to 5 was attached, were actually used to alternately measure blood pressures of the same person 10 times each.

Here, the upper-arm blood pressure monitor Model HEM-7120 manufactured by Omron Healthcare Co., Ltd. was used as the upper-arm blood pressure monitor. The upper-arm blood pressure monitor was worn on the wrist, and the blood pressure monitor 1 according to the examples and its comparative examples was worn on the wrist. The bag-shaped structure 32 of which the standard deviation of differences between the blood pressure values of the 10-time measurements was 7 mmHg or higher was regarded as having bad vascular compressibility and achieving low measurement precision, and determined as "not good", while the bag-shaped structure 32 of which the standard deviation fell below 7 mmHg was regarded as having good vascular compressibility and achieving high measurement precision, and determined as "good".

[Evaluation Test 3]

For Evaluation Test 3, a repeated-use durability evaluation test was performed for the bag-shaped structures 32 according to Examples 1 to 7 and Comparative Examples 1 to 5.

In the repeated-use durability evaluation test, the blood pressure monitor 1, to which each of the bag-shaped structures 32 produced in Examples 1 to 7 and Comparative Examples 1 to 5 was attached, was inflated until the inner pressure of the bag-shaped structure 32 reached a pressure of 300 mmHg, and then the pressure was reduced to deflate the blood pressure monitor 1. This process was repeated 10,000 times. An amount of slack was measured based on extension of the bag-shaped structure 32 after the repetition of 10,000 times of inflation and deflation, with respect to the state before the inflation and deflation, and the bag-shaped structure 32 was determined as "not good" if the amount of slack reaches 5% or higher, and was determined as "good" if the amount of slack falls below 5%.

[Results of Evaluation Tests]

The results of the Evaluation Tests 1 to 3 are shown in Tables 1 and 2. To clarify the results of the evaluation tests, Table 1 shows the evaluations results of Examples 1 to 4 and Comparative Example 3, in which the bag-shaped structure 32 included a plurality of layers having the same layer composition ratio, and evaluation results of Comparative Examples 1 and 2 in which the bag-shaped structure 32 had a single-layer structure. For the same reason, Table 2 shows the results of evaluation tests of Example 2, Examples 5-7, and Comparative Examples 4 and 5 in which a plurality of layers were formed of the same material, and had different layer composition ratios.

TABLE 1

|  | TACTILE SENSATION | VASCULAR COMPRESSIBILITY RESULT | STANDARD DEVIATION | REPEATED-USE DURABILITY RESULT | EXTENSION |
|---|---|---|---|---|---|
| EXAMPLE 1 | GOOD | GOOD | 6 mmHg | GOOD | 4% EXTENSION |
| EXAMPLE 2 | GOOD | GOOD | 3 mmHg | GOOD | 1% EXTENSION |
| EXAMPLE 3 | GOOD | GOOD | 4 mmHg | GOOD | 2% EXTENSION |
| EXAMPLE 4 | GOOD | GOOD | 3 mmHg | GOOD | 1% EXTENSION |
| COMPARATIVE EXAMPLE 1 | NOT GOOD | NOT GOOD | 10 mmHg | NOT GOOD | 7% EXTENSION |
| COMPARATIVE EXAMPLE 2 | GOOD | NOT GOOD | 8 mmHg | GOOD | 3% EXTENSION |
| COMPARATIVE EXAMPLE 3 | NOT GOOD | NOT GOOD | 10 mmHg | NOT GOOD | 6% EXTENSION |

As shown in Table 1, in Examples 1 to 4, all of the tactile sensation of Evaluation Test 1, the vascular compressibility of Evaluation Test 2, and the repeated-use durability in Evaluation Test 3 were determined as "good".

On the other hand, in Comparative Example 1, all of the tactile sensation of Evaluation Test 1, the vascular compressibility of Evaluation Test 2, and the repeated-use durability of Evaluation Test 3 were "not good". Being formed of a single-layer sheet of a soft TPU material having a Shore A hardness of 65, the bag-shaped structure of Comparative Example 1 exhibited adhesiveness, and thus would have decreased the tactile sensation to the human skin. In addition, such adhesiveness would have decreased the conformability to the human skin surface and the vascular compressibility when the bag-shaped structure was inflated, and also compressed the living body. This is considered to be the reason for the above results. In addition, since the Shore A hardness was as low as 65, the creep resistance, which represents the repeated-use durability of the bag-shaped structure, would also have reduced.

In Comparative Example 2, the tactile sensation in Evaluation Test 1 and the repeated-use durability of Evaluation Test 3 were determined as "good"; however, the vascular compressibility in Evaluation Test 2 were determined as "not good". Being formed of a relatively hard material having a Shore A hardness of 70, the bag-shaped structure of Comparative Example 2 did not exhibit adhesiveness and caused little slack resulting from creep. However, when the bag-shaped structure of Comparative Example 2 was inflated and compressed the living body, the conformability to the human skin would have been low, resulting in a decrease in vascular compressibility. This is considered to be the reason for the above results.

In Comparative Example 3, all of the tactile sensation in Evaluation Test 1, the vascular compressibility in Evaluation Test 2, and the repeated-use durability in Evaluation test 3 were determined as "not good". Comparative Example 3 had a layer configuration in which the first sheet member and the second sheet member had a two-type, three-layer structure, which is opposite to the layer configuration of the two-type, three-layer structure of the first sheet member 41 and the second sheet member 42 according to the embodiment. Thus, the outer layer of the bag-shaped structure of Comparative Example 3 was formed of soft TPU having a Shore A hardness of 65, which gave the outer surface of the bag-shaped structure adhesiveness. This would have resulted in a decrease in tactile sensation, vascular compressibility, and repeated-use durability. This is considered to be the reason for the above results.

TABLE 2

|  | TACTILE SENSATION | VASCULAR COMPRESSIBILITY RESULT | STANDARD DEVIATION | REPEATED-USE DURABILITY RESULT | EXTENSION |
|---|---|---|---|---|---|
| EXAMPLE 2 | GOOD | GOOD | 3 mmHg | GOOD | 1% EXTENSION |
| EXAMPLE 5 | GOOD | GOOD | 6 mmHg | GOOD | 1% EXTENSION |
| EXAMPLE 6 | GOOD | GOOD | 5 mmHg | GOOD | 1% EXTENSION |
| EXAMPLE 7 | GOOD | GOOD | 4 mmHg | GOOD | 3% EXTENSION |
| EXAMPLE 8 | GOOD | GOOD | 3 mmHg | GOOD | 4% EXTENSION |
| COMPARATIVE EXAMPLE 4 | GOOD | NOT GOOD | 22 mmHg | GOOD | 1% EXTENSION |
| COMPARATIVE EXAMPLE 5 | GOOD | GOOD | 3 mmHg | NOT GOOD | 6% EXTENSION |

As shown in Table 2, in Example 2 and 5 to 7, all of the tactile sensation in Evaluation Test 1, the vascular compressibility in Evaluation Test 2, and the repeated-use durability in Evaluation Test 3 were determined as "good".

On the other hand, in Comparative Example 4, the tactile sensation in Evaluation Test 1 and the repeated-use durability in Evaluation Test 3 were determined as "good"; however, the vascular compressibility in Evaluation Test 2 was determined as "not good". The bag-shaped structure of Comparative Example 4 was configured in such a manner that the first sheet member and the second sheet member had a layer composition ratio represented by $T1a:T2b:T1c=1:1:1$, and the second layers 41b and 42b, forming the inner layers, formed a small proportion of the total thickness of the first sheet member and the second sheet member. Thus, since the inner layers formed a small proportion in the bag-shaped structure of Comparative Example 4, the physical properties of the outer layers, i.e., the first layers 41a and 42a and the third layers 41c and 42c were dominant. Consequently, the bag-shaped structure of Comparative Example 4 was rigid, did not exhibit adhesiveness, and caused little slack resulting from creep. However, the bag-shaped structure of Comparative Example 4 did not exhibit flexibility, and thus would have decreased the conformability to the human skin surface when the bag-shaped structure was inflated and compressed the living body. This would have resulted in a decrease in vascular compressibility of the bag-shaped structure of Comparative Example 4. This is considered to be the reason for the above results.

In Comparative Example 5, the tactile sensation in Evaluation Test 1 and the vascular compressibility in Evaluation Test 2 were determined as "good"; however, the repeated-use durability in Evaluation Test 3 was determined as "not good". The bag-shaped structure of Comparative Example 5 was configured in such a manner that the first sheet member and the second sheet member had a layer composition ratio represented by $T1a:T2b:T1c=1:25:1$, and the second layers 41b and 42b, forming the inner layers, formed a large proportion of the total thickness of the first sheet member and the second sheet member. Thus, in the bag-shaped structure of Comparative Example 5, the physical properties of the first layers 41a and 42a and the third layers 41c and 42c, forming the outer layers, hardly make a contribution, causing the first sheet member and the second sheet member to be soft. Consequently, the bag-shaped structure of Comparative Example 5 did not exhibit adhesiveness, and would have had high conformability to the human skin surface when the bag-shaped structure was inflated and compressed the living body. However, in the bag-shaped structure of Comparative Example 5, slack resulting from creep would have increased. This is considered to be the reason for the above results.

From these results, it can be seen that, by configuring the bag-shaped structure 32 used for the cuff 12 of the blood pressure monitor 1 according to the above-described embodiment and its modifications, it is possible to achieve both high creep resistance and flexibility, and to have appropriate functions as the cuff 12 of the blood pressure monitor 1. It can also be seen that, by forming the bag-shaped structure 32 by joining two members, namely, the first sheet member 41 and the second sheet member 42, it is possible to reduce the processing cost while providing such appropriate functions.

The invention claimed is:

1. A bag-shaped structure comprising:
    a first sheet member including a layer formed of a thermoplastic elastomer; and
    a second sheet member including a plurality of layers formed of a plurality of types of thermoplastic elastomers having different levels of hardness, wherein
    the second sheet member is joined with the first sheet member,
    a layer that is included in the plurality of layers of the second sheet member, and that is in contact with a living body, has a Shore A hardness higher than a Shore A hardness of at least one of the other layers of the second sheet member; and
    wherein the second sheet includes a first layer that is in contact with the living body, a second layer that is in contact with the first sheet member, and a third layer that is included between the first layer and the second layer, the third layer having a Shore A hardness lower than a Shore A hardness of the first and second layers.

2. The bag-shaped structure according to claim 1, wherein the first layer and the second layer are formed to have the same thickness, and
    the second sheet member is configured to have a layer composition ratio T1:T2:T1 ranging between 1:2:1 and 1:20:1, where T1 represents a thickness of each of the first layer and the second layer, and T2 represents a thickness of the third layer.

3. The bag-shaped structure according to claim 1, wherein the second sheet member is configured in such a manner that the first layer and the second layer are formed of a thermoplastic elastomer having a Shore A hardness of 70 or higher, and the third layer is formed of a thermoplastic elastomer having a Shore A hardness of 65 or lower.

4. The bag-shaped structure according to claim 1, wherein the thermoplastic elastomer is formed of a thermoplastic polyurethane resin.

* * * * *